(12) United States Patent
Goldbach

(10) Patent No.: US 8,096,163 B2
(45) Date of Patent: Jan. 17, 2012

(54) VERIFYING THE CALIBRATION STATUS OF AN OPTICAL TRACKING SYSTEM

(75) Inventor: Gunter Goldbach, Wifling (DE)

(73) Assignee: Brainlab AG, Feldkirchen (DE)

( * ) Notice: Subject to any disclaimer, the term of this patent is extended or adjusted under 35 U.S.C. 154(b) by 646 days.

(21) Appl. No.: 12/262,235

(22) Filed: Oct. 31, 2008

(65) Prior Publication Data

US 2009/0113986 A1    May 7, 2009

Related U.S. Application Data

(60) Provisional application No. 60/987,600, filed on Nov. 13, 2007.

(30) Foreign Application Priority Data

Oct. 31, 2007 (EP) .................................... 07119752

(51) Int. Cl.
*G01B 3/30* (2006.01)
(52) U.S. Cl. ........................................................ 73/1.79
(58) Field of Classification Search .................. None
See application file for complete search history.

(56) References Cited

U.S. PATENT DOCUMENTS

2005/0203374 A1   9/2005   Vilsmeier
2005/0215879 A1   9/2005   Chuanggui

FOREIGN PATENT DOCUMENTS

EP        1 184 684       3/2002
EP        1 769 768       4/2007
WO      2005/102202    11/2005

*Primary Examiner* — Robert Raevis
(74) *Attorney, Agent, or Firm* — Renner, Otto, Boisselle & Sklar, LLP

(57) ABSTRACT

The invention relates to a method for verifying the calibration status of an optical tracking system (1), wherein:

a calibration apparatus (20, 40), which comprises a tracking marker configuration (27, 28; 41, 42), is moved to within the detection range of the tracking system (1);

the tracking markers (27, 28; 41, 42) of the calibration apparatus (20, 40) are detected by the tracking system;

the arrangement of the tracking markers (27, 28; 41, 42) is changed and/or moved into a state such that the tracking system (1) experiences a detection problem;

the arrangement of the tracking markers (27, 28; 41, 42) which causes the detection problem is gauged and/or a range of arrangements for the tracking markers (27, 28; 41, 42) which causes the detection problem is gauged; and the tracking system (1) is determined to have a calibration error when the gauged arrangement and/or range of arrangements does not have a predetermined value or is not within a predetermined range of values.

It also relates to a device for verifying the calibration status of an optical tracking system (1).

20 Claims, 4 Drawing Sheets

VERIFYING THE CALIBRATION STATUS OF AN OPTICAL TRACKING SYSTEM

RELATED APPLICATION DATA

This application claims priority of U.S. Provisional Application No. 60/987,600 filed on Nov. 13, 2007, which is incorporated herein by reference in its entirety.

FIELD OF THE INVENTION

The invention relates to verifying the calibration status of an optical tracking system. The invention is in particular used in the field of medically used and/or medical optical tracking systems which serve to ascertain the spatial position of tracking markers (for example, on medical instruments or apparatus and/or on patients) and provide these to medical navigation systems, in order to be able to perform image-guided surgery and/or treatment.

BACKGROUND OF THE INVENTION

Known, commercially available tracking systems of this type are delivered pre-calibrated, i.e. the exact parameters of the arrangement of their components are known and are taken into account when ascertaining spatial co-ordinates for tracking markers. One general problem with such stereoscopic tracking systems which are pre-calibrated when they are manufactured is that of verifying the stability of the calibration over a longer period of use ("in the field"). Aside from a few very basic functional tests, there is no way of checking the accuracy of the known systems. However, since medical applications of such tracking systems increasingly have accuracy requirements in the sub-millimeter range, verifying the accuracy and/or calibration status is becoming more and more important.

Currently, tracking systems are in most cases checked annually with the aid of a large co-ordinate gauging system which is typically also used for calibrating such systems. However, this cannot be performed in the field, i.e. in situ where the user is; rather, the tracking systems have to be delivered to the manufacturer, where such a co-ordinate gauging system is available. This is associated with a great deal of effort and in particular high costs, and the systems are not available to the user for the corresponding period of time. At the manufacturer's, or wherever the calibration can be performed, the tested device is gauged on the basis of a substantially better (typically, ten times better) reference standard and is possibly recalibrated. However, because the accuracy and stability of the tracking systems are gaining ever-greater importance, because the manufacturer's calibrations mentioned or recalibrations are expensive and incur a downtime, and because non-calibrated systems incur the danger of treatment errors, it is exceedingly important to enable the calibration status of the optical tracking system to be verified in situ where the user is, and with as little effort as possible.

SUMMARY OF THE INVENTION

This is the object of the present invention.
The object mentioned is solved by a method for verifying the calibration status of an optical tracking system in accordance with claim 1 and by a device, provided for this purpose, in accordance with claim 12. The sub-claims define preferred embodiments of the invention.

In the method in accordance with the invention for verifying the calibration status of an optical tracking system, the following steps are performed:
- a calibration apparatus, which comprises a tracking marker configuration, is moved to within the detection range of the tracking system;
- the tracking markers of the calibration apparatus are detected by the tracking system;
- the arrangement of the tracking markers is changed and/or moved into a state such that the tracking system experiences a detection problem;
- the arrangement of the tracking markers which causes the detection problem is gauged and/or a range of arrangements for the tracking markers which causes the detection problem is gauged; and
- the tracking system is determined to have a calibration error when the gauged arrangement and/or range of arrangements does not have a predetermined value or is not within a predetermined range of values.

In other words, the present invention utilizes the fact that in some cases, tracking systems have problems with correctly detecting tracking markers. In accordance with the invention, a check is made as to whether there are any problems, specifically how significant these problems are and/or were, and how long they occur for, and from this information, it is conversely possible to deduce the calibration status of the tracking system, since the corresponding detection problems occur when the calibration deteriorates, i.e. the invention makes "a virtue of necessity", by using precisely those detection errors such as may occur to draw conclusions about the calibration quality of a tracking system. These conclusions can be qualitative in nature (calibrated / non-calibrated); however, it is also possible to make quantitative statements about the extent of calibration errors.

The invention substantially simplifies verifying the calibration of a tracking system, and can be performed by the user himself or by a service technician with a rudimentary level of training. The tools and/or calibration apparatus used can be provided at low cost and in a robust manner for use in situ. Ascertaining the calibration status is not dependent on specific embodiments, versions, manufacturers or revisions of stereoscopic tracking systems, since it relates to fundamental physical parameters which obtain for any tracking system. The same test can thus be used with many different tracking systems.

In accordance with one embodiment in accordance with the invention, the arrangement of the tracking markers can be gauged by a measuring means which is assigned or attached to the calibration apparatus. The measurement results from gauging the arrangement of the tracking markers can also be directly read off on the measuring means or the calibration apparatus, wherein scales or value indicators are arranged on the calibration apparatus in particular. Using these embodiments, verification can be performed quickly, immediately and directly with the aid of the calibration apparatus.

In one embodiment variant of the method in accordance with the invention, only simple geometric relationships such as distances or angular positions are measured when gauging the arrangement of the tracking markers, wherein simple geometric relationships are those which can be palpably measured with little effort or using means which are easy to acquire, whereby verifying in accordance with the invention may be attributed to the simplest measuring processes which can be performed at any time and anywhere.

When comparing the arrangement and/or range of arrangements with the predetermined value and/or range of values, arrangements of the tracking markers relative to each other or arrangements of the tracking marker configuration relative to each other can be adduced. One advantage of such an embodiment is that it is not necessary to set any absolute points or angles or the like, i.e. zero points or zero positions, in the detection range of the tracking system. The invention does not however exclude the possibility of comparisons with absolute values, ranges of values or arrangements.

One detection problem with tracking systems which can be used in the present invention is the occurrence of ambiguities in detecting markers, wherein the number of detected potential tracking markers is greater than the number of tracking markers actually present in the detection range, wherein the arrangement of the tracking marker configuration for generating the occurrence of the ambiguities is set such that the tracking markers are situated substantially in the epipolar plane of the tracking system. One way of performing the method is then to pivot the tracking marker configuration substantially perpendicular to the epipolar plane and to use the measuring means to determine the angular range within which the ambiguities occur. When the angle determined in this way is greater than a predetermined angular range, the tracking system can be determined to have a calibration error. Depending on how much greater the determined angular range is, it is also possible to make a quantitative statement about the calibration error.

Another detection problem which can be adduced in the course of performing the present invention is the occurrence of an insufficient resolution of individual markers when detecting markers, wherein for two tracking markers which are actually present and have a small distance from each other, the tracking system only detects a single marker.

In this respect, it is possible to move the calibration apparatus for detecting markers to a predetermined point within the detection range of the tracking system, in particular to a predetermined distance from the tracking system, in order to obtain comparable and/or highly informative values. If the latter embodiment mentioned above is chosen, the arrangement of the tracking markers for generating the occurrence of the insufficient resolution of individual markers can be changed such that the distance between the tracking markers is reduced. Using the measuring means, it is possible to determine the distance between the tracking markers at which the individual resolution is insufficient, and if this distance is greater than a predetermined maximum distance, the tracking system can be determined to have a calibration error.

A device in accordance with the invention for verifying the calibration status of an optical tracking system comprises:
  a calibration apparatus which comprises a tracking marker configuration;
  a tracking marker movement device, by means of which the arrangement of the tracking markers can be changed and/or moved into a state such that the tracking system experiences a detection problem;
  a measuring means, using which the arrangement of the tracking markers which causes the detection problem is gauged and/or a range of arrangements for the tracking markers which causes the detection problem is gauged; and
  an evaluation unit in which, when the gauged arrangement and/or range of arrangements does not have a predetermined value or is not within a predetermined range of values, the tracking system is determined to have a calibration error.

The evaluation unit mentioned can be a computer-assisted evaluation unit connected to the tracking system and/or to the calibration apparatus; it can be provided with such a function separately, or can also be integrated into a system already present in situ, for example into a medical navigation system.

The measuring means can be assigned or attached to the calibration apparatus and can also comprise a display on which measurement results from gauging the arrangement of the tracking markers can be read off, wherein scales or value indicators are arranged on the calibration apparatus in particular. It is of course also possible to output the measurement results, possibly together with the detection results of the tracking system, on a separate display assigned to the evaluation unit or to a navigation system. Corresponding data connections can be provided by cables or wirelessly.

The measuring means is preferably a measuring means which measures simple geometric relationships such as distances or angular positions, wherein the advantages already mentioned above arise.

If the detection problem is the occurrence of ambiguities, the device can be configured such that the tracking markers—in particular, two tracking markers—are attached at a distance on a mounting which is arranged on the calibration apparatus such that it can pivot, wherein an angular scale is preferably also provided on the calibration apparatus, for indicating the pivoting angle of the mounting or of the marker configuration.

If the detection problem is the occurrence of an insufficient resolution of individual markers when detecting markers, the device can be embodied such that the tracking markers—in particular, two tracking markers—are attached at a distance on a mounting, wherein an adjusting device is provided for the distance between the tracking markers, wherein in accordance with one embodiment variant, the calibration apparatus comprises a rail, and at least one tracking marker is arranged such that it can be displaced on the rail, wherein the distance is measured on the basis of the displacement path on the rail.

It may also be stated that the occurrence of ambiguities and the occurrence of an insufficient resolution of individual markers are merely examples of detection problems which can be used in connection with the present invention. Any other conceivable detection problems which can at least partially indicate a loss of calibration on a tracking system can be used in accordance with the invention.

BRIEF DESCRIPTION OF THE DRAWINGS

The invention is illustrated in more detail below on the basis of example embodiments. It can include any of the features described here, individually and in any expedient combination. The drawings show.

The present invention, using which the calibration status of an optical stereoscopic tracking system can be ascertained without having to know the internal calibration parameters (for example, camera parameters) or the underlying calibration model, is illustrated in more detail below. For better comprehension, however, a description shall also be given first, of how a stereoscopic three-dimensional tracking system operates.

DETAILED DESCRIPTION OF THE INVENTION

Figure 1:
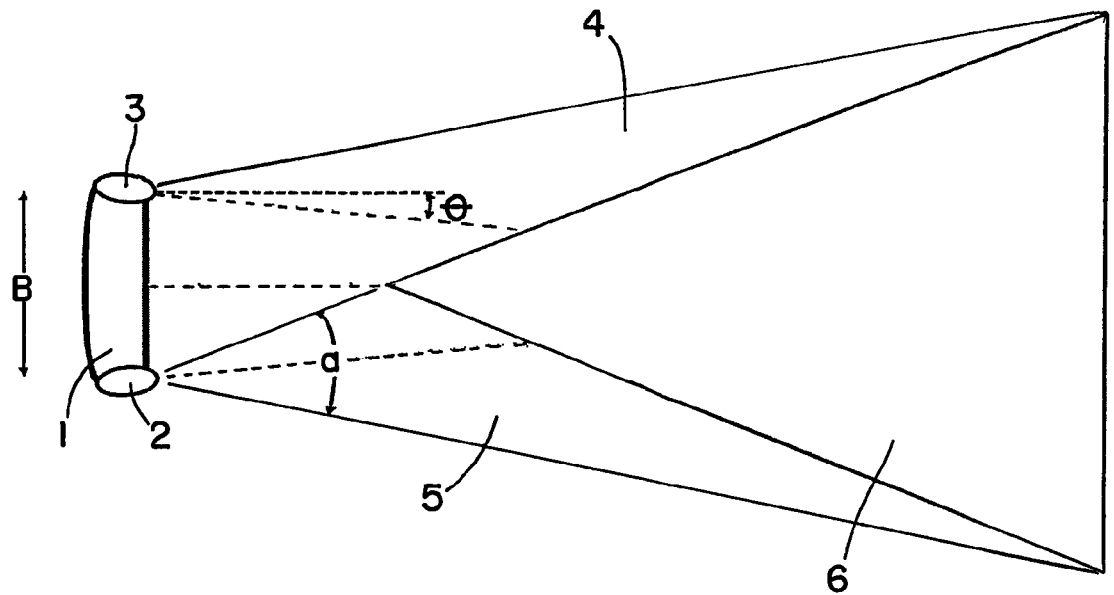
FIGS. 1 and 2 representations which illustrate the basic mode of operation of an optical stereoscopic tracking system.
Figure 2:
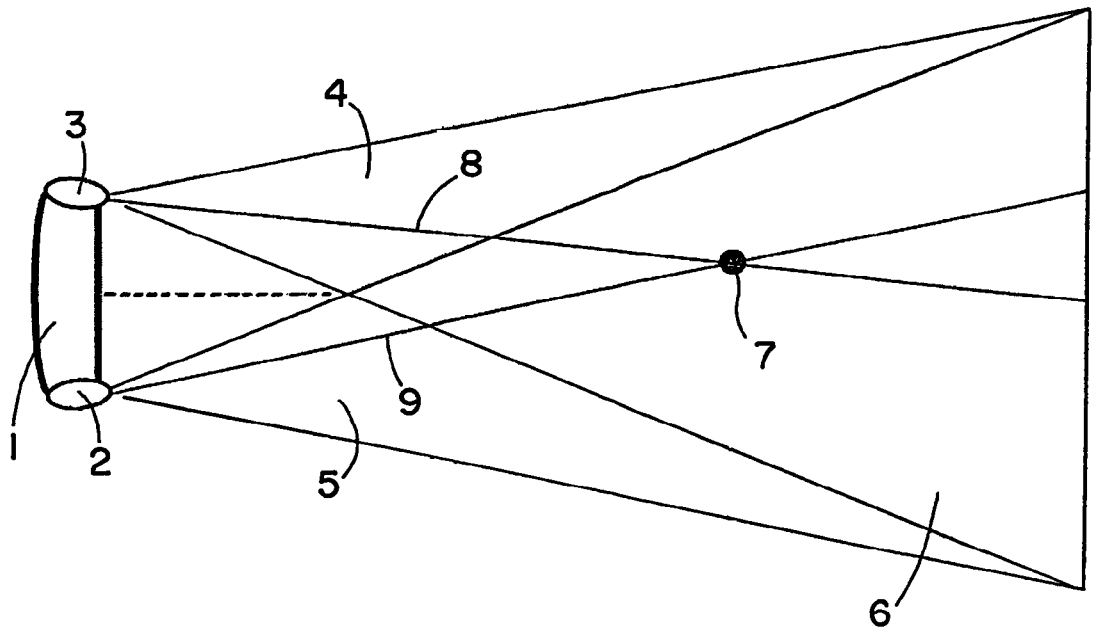

In FIGS. 1 and 2, a tracking system bears the reference sign 1 and comprises two cameras and/or sensors 2, 3. These two cameras or region sensors (typically, CCD or CMOS sensors) record images at a particular angle of view. The distance between the two cameras (sensors) 2, 3 is referred to as the base distance B. The angle $\Phi$ (phi) describes the angle of inclination which allows the overlap of the two fields of view 4, 5 to be set which results in the detection range 6. The angle $\alpha$ (alpha) describes the angle of view of each sensor and/or camera (optical system). For many stereoscopic systems which are used for medical image-guided surgery, the base distance B is in the range of 150 mm to 1000 mm, and the angle $\Phi$ is in the range of 0 to 20 degrees. The angle of view $\alpha$ of each sensor is typically in the range of 10 to 80 degrees.

The calibration of the system then defines the exact parameters of the physical arrangement of the two sensors with respect to each other (distance, inclination, rotation, torsion, etc.). These parameters are often referred to as "external calibration parameters", since they define the external relationship between the sensors. In addition to these external parameters, "internal parameters" of each sensor arrangement are also incorporated into the calibration (for example, the focal length, curvature of the lens, alignment, epicenter, etc.).

The internal parameters can be set very precisely and kept stable by a stable hardware design. The external parameters, however, are subject to often significant changes due to specific stresses, for example changes in temperature, mechanical impacts, changes in humidity, material fatigue, material dilation due to gravity (depending on the setup of the system) and other environmental influences. Attempts are therefore made when manufacturing pre-calibrated tracking systems to keep the changes in the external parameters small using design measures, so as to be able to ensure a specific accuracy over a longer period of time.

Critical conditions are for example created when the system is transported from the manufacturer to the end consumer or when handled by the end consumer (dropping, impacting). It is not then easy for the end consumer to determine whether such an incident has damaged the system or affected the specifications.

For many medical applications, the required accuracy for three-dimensional marker positions reaches values of 0.1 to 1 mm in large detection ranges (compared to the size of the stereoscopic system and/or its base distance B). The calibrated volume is typically in the range of 1 to 5 m, at a base distance of 50 to 80 cm. This results in maximum admissible changes in the external calibration parameters of the order of only a few micrometers, a few millidegrees or even less. A calibrated system detects a marker in the detection range 6 (FIG. 2) by calculating the three-dimensional position from the image position of the marker 7 on each sensor 2, 3 (view ray 9, 8) and from the known (calibrated) relationship between the sensors 2, 3 (triangulation). Ideally, the two view rays 9, 8 for the marker 7 intersect at exactly one point and so render the true marker position. Due to tolerances, image processing artifacts and other uncertainties, a certain tolerance has to be allowed when predicting the marker position.

If, as shown in FIG. 2, only one marker is to be detected, this has the advantage that the rays 8 and 9 only have one intersection point, which simplifies triangulation. In actual applications, however, a single three-dimensional marker position would not allow the alignment of an object to be determined or a medical instrument to be navigated. A number of markers therefore have to be detected, and the relative distances allow six-dimensional information for rigid bodies or three-dimensional distances of the markers and instruments relative to each other to be ascertained.

Figure 3:
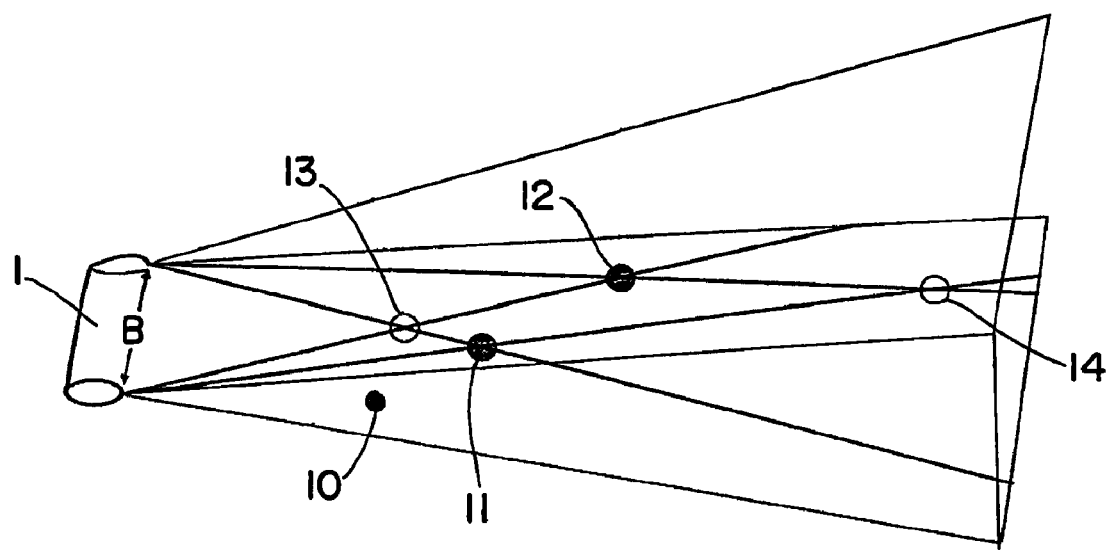
FIG. 3 a representation which illustrates the occurrence of ambiguities when detecting tracking markers.

In many practical applications, only one intersection point is actually created for two view rays in the three-dimensional detection field of the tracking system, whereby the marker positions can then be ascertained. If, however, the markers are arranged within a plane parallel to the base B (epipolar plane), a number of markers in this plane would cause ambiguities, since a number of possible intersection points occur. Such a case is shown in FIG. 3, in which the epipolar plane is indicated by the reference sign 10. Two actual markers 11, 12 lie in this epipolar plane, but the triangulation process would result in four potential markers, i.e. two additional markers 13 and 14 which are not actually present, since the view rays from each camera intersect a total of four times. If the number of markers in a plane parallel to the base B is n, the number of ambiguities increases by $n^2$.

If possible, the described problem with ambiguities is solved by comparing the marker sizes, marker luminosities or other properties, in order to be able to perform navigation. However, this requires a relatively large image processing and computational effort.

The present invention uses, among other things, precisely the fact that such ambiguity problems can occur for verifying the tracking system calibration, i.e. the "ability" of the tracking system to produce such ambiguities is used as a quality criterion for the tracking system. A well-calibrated system would generate ambiguities within only a very small range, i.e. when the tracking markers lie very exactly parallel to the base B. Using a simple tool (for example, a pointer tool comprising two tracking markers) and rotating the tool perpendicular to the epipolar plane can result in a range of inclination for the two markers, within which ambiguities are generated. A well-calibrated system would have only a very small such range, while a more poorly calibrated and/or inaccurate system would exhibit a larger range. An ambiguity angle $\beta$ can thus be defined which can be used as a quality criterion for testing tracking systems in situ where the user is.

As already mentioned above, the ambiguity angle $\beta$ can be ascertained using a simple tool which comprises two tracking markers. The absolute angular arrangement of the tool and/or tracking markers also plays a direct part in determining the angle, because it can be ascertained on the basis of the question of what the maximum angular range is, within which the two markers generate ambiguities. Ideally, the system would only have a very small inclination (a small ambiguity angle). The angle $\beta$ may or may not vary within the detection volume, depending on the internal system parameters and the underlying calibration model. In a known system, specifications for the angle $\beta$ can be given or can be ascertained by the user, and changes can be easily detected by means of the simple tool.

Figure 4:
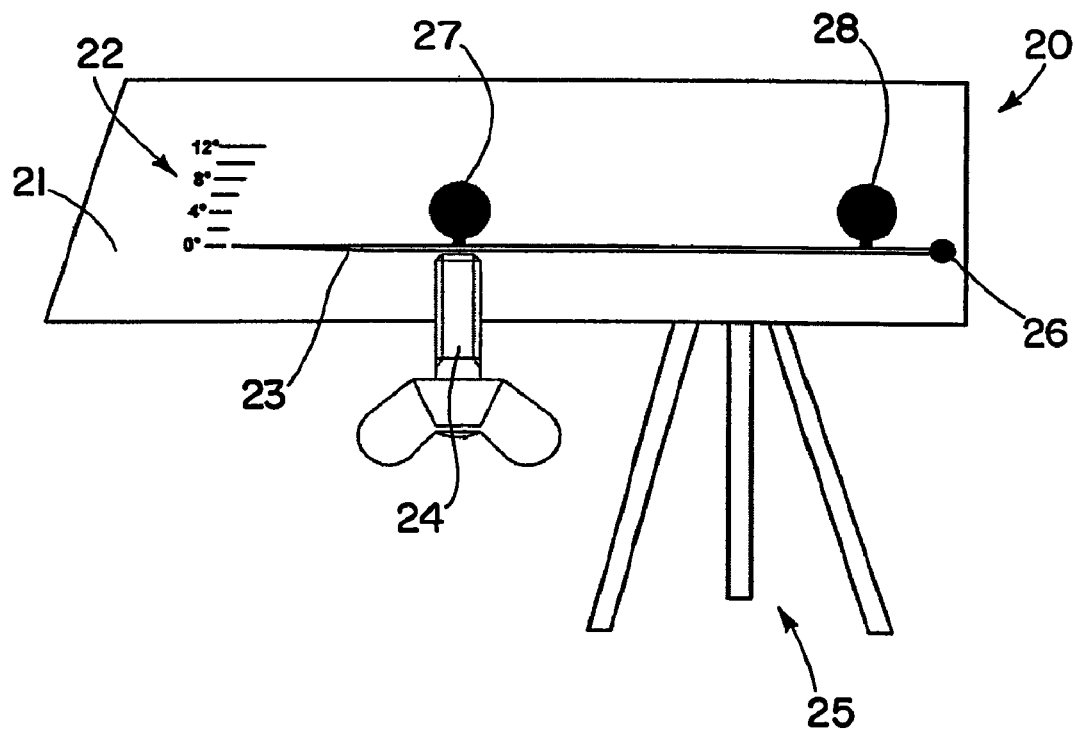
FIG. 4 a device in accordance with the invention, in a first embodiment.

One embodiment of such a calibration apparatus (apparatus for checking the calibration) is shown in FIG. 4. The calibration apparatus 20 of FIG. 4 stands on three support legs 25 and comprises a back plate 21 onto which an angular scale is attached. An indicator needle 23 is mounted at the pivot point 26, and two tracking markers 27 and 28 are positioned at a distance on the indicator needle. The inclination of the needle 23 can be set using the setting screw 24.

The angle of the needle 23 can then be changed using this simple configuration, and the minimum and maximum angle at which ambiguities occur can be read off via the scale 22.

Because a simple subtraction then yields the ambiguity angle β, it is not even necessary in this approach for the initial angle with respect to the epipolar plane to be known. It is sufficient in this case if absolute spatial angular values are not ascertained, but only relative values which then provide sufficient information about the ambiguity angle β. Other embodiments are possible, and could include a calibration apparatus which generates one or two laser lines which can be aligned with the base B of the tracking system. The angle β can be measured by rotating the apparatus with the second laser, and by determining the angular relationship between the two laser lines.

One major advantage of this calibration evaluation is that it is completely independent of the type of tracking system; it is merely necessary to check whether the tracking system relays more than two expected marker positions, and then define the range within which this is and/or may be possible.

Figure 5:
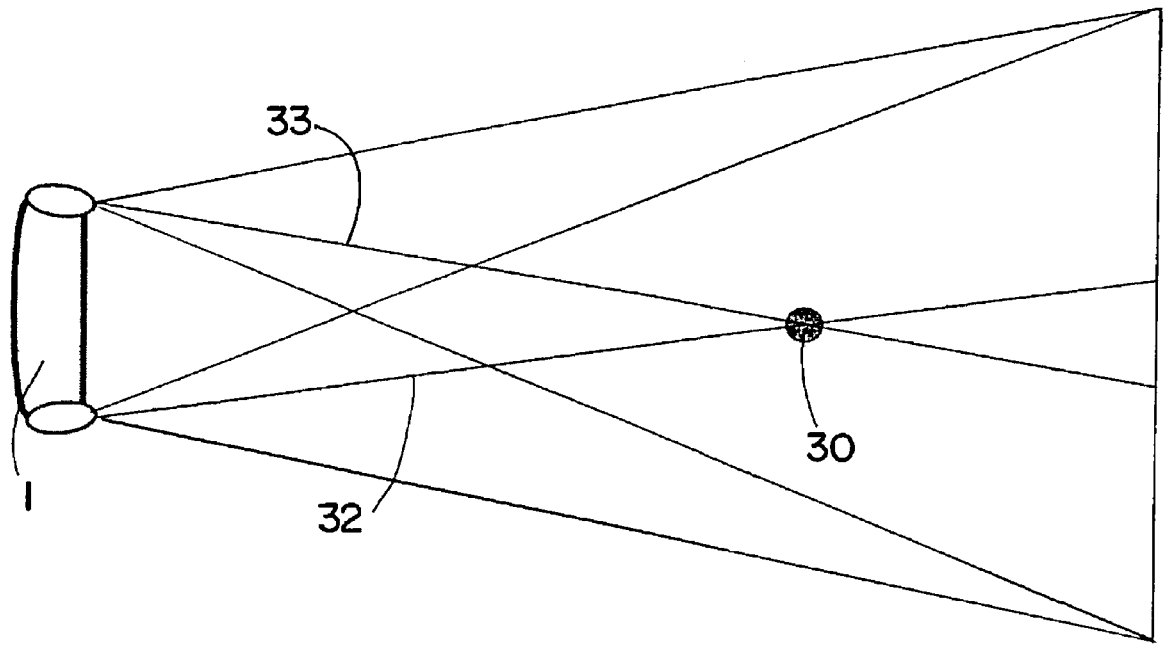
FIGS. 5 and 6 representations which illustrate a mode of operation of a tracking system in conjunction with occurring ray deviations.
Figure 6:
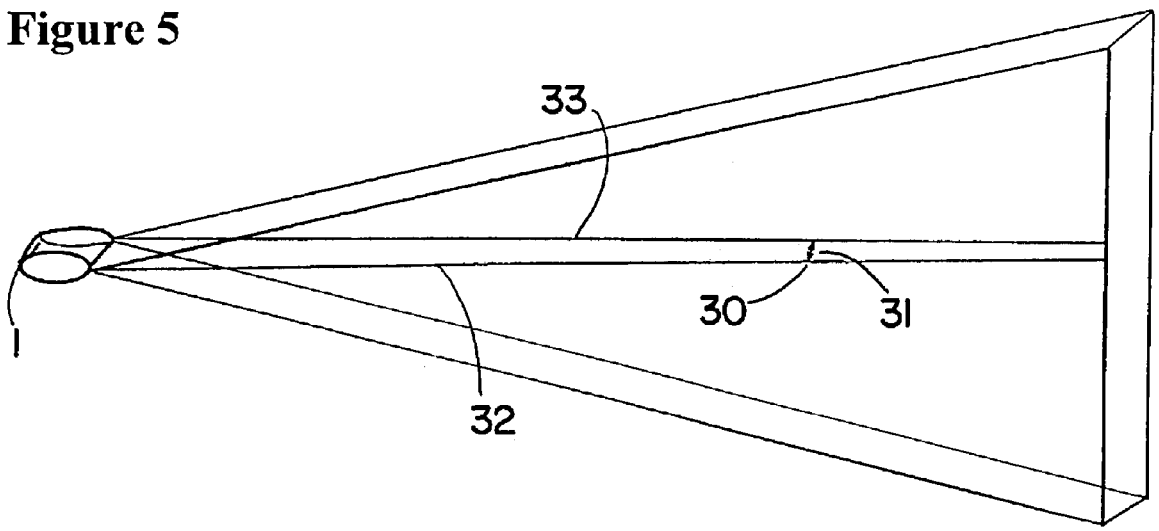

Another embodiment of the present invention employs ray deviations and the so-called resolution of individual markers. It has already been mentioned above that the two view rays ideally intersect at exactly one point which indicates the marker position, but that due to tolerances, image processing artifacts, distortions and other uncertainties, a certain tolerance has to be allowed when detecting the marker position. This tolerance range is referred to as "ray deviation". It should be noted that this is not just a two-dimensional distance but rather a three-dimensional distance, namely the minimum spatial distance between the two view rays. The ray deviation of each marker is basically a vector having one direction (the minimum distance between one ray and the other). Due to the geometric properties of the triangulation system and the underlying projection model, defining a ray deviation is expedient and is also typically to be found in the literature. FIGS. 5 and 6 show, in a view from above (FIG. 5) and in a lateral view (FIG. 6), how the two view rays 32, 33 intersect at a marker 30, subject to a tolerance. In the view from above in FIG. 5, the two rays 32, 33 appear to intersect directly on the marker; however, the lateral view in FIG. 6 shows that the two rays are slightly offset spatially (skewed) with respect to each other, and the minimum spatial distance between the two rays is indicated by the reference sign 31.

The ray deviation distance or ray deviation angle is by its very nature a useful internal parameter for confirming the quality in detecting markers, and in turn results in a quality criterion for the calibration. If the ray deviation distance is too large, an alignment error of the sensor system may be assumed, and the overall calibration of the system has very probably been lost. For tracking systems, a maximum value for the ray deviation at an individual marker point is typically defined, and marker positions which do not fall within this range are not used. Since an alignment error of the sensors typically only results in an increased ray deviation angle, a typical effect of such decalibrated systems is that marker positions can no longer be detected over the entire detection volume, but rather typically at smaller distances from the tracking system or in mid-ranges of the tracking volume. The user can therefore easily make a rough determination of the performance of the system, by checking whether markers can still be tracked at the near or far end of the calibrated volume.

If the ray deviation is still within a specified range, it is not suitable for checking the calibration, and this also applies when it is not possible to ascertain the ray deviation for commercially available systems. In this case, the present invention expands the ray deviation scenario by using a marker configuration, i.e. by using more than one marker in a specific arrangement, and so falls back on a specific parameter of stereoscopic tracking systems referred to as the "resolution of individual markers". This term defines the ability of a tracking system to differentiate between two individual markers which are near each other. If the distance between the two markers becomes smaller, the system will at some point no longer be capable of differentiating between the markers. This results either in only one marker being detected, or —due to internal criteria such as an expected marker shape or a minimum distance criterion—in no marker being detected.

On the basis of the fact that the marker resolution cannot be higher than the ray deviation which is allowed in the system, it may be expected that the minimum marker distance between two markers is not constant over the spatial arrangement of the two markers. It will change with the distance from the sensor unit.

For a predetermined spatial distance from the tracking system, however, the minimum distance between the two markers can be detected such that it provides valuable information about the accuracy of the system and allows the user to evaluate the calibration.

Figure 7:
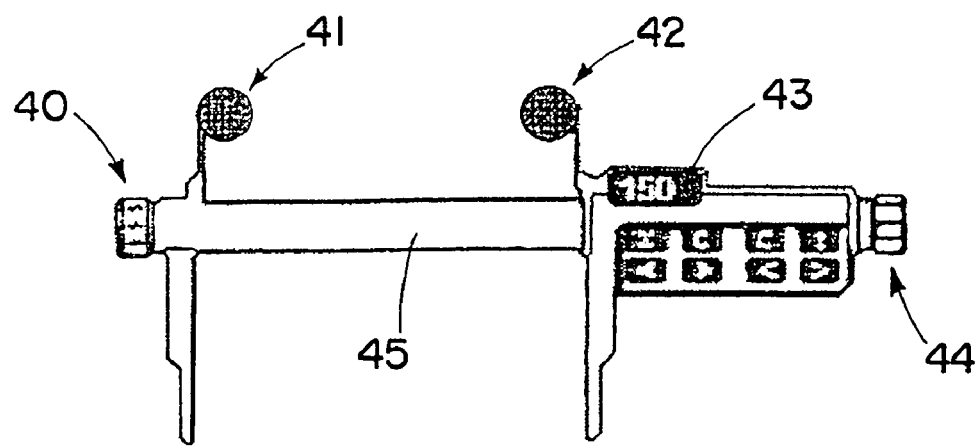
FIG. 7 a second embodiment of a device in accordance with the invention.

An apparatus such as is shown in FIG. 7 and which as a whole bears the reference sign 40 can then be used as the calibration apparatus (apparatus for checking the calibration). The apparatus 40 is basically configured as a sliding rule comprising a rail 45, an electronic distance indicator 43 and manual/electric adjusting devices 44. It bears the two tracking markers 41 and 42, and the distance between the two markers (centre distance) is indicated on the display 43. It is thus possible to read off on the calibration apparatus 40 exactly how far apart the markers 41 and 42 are, and to then check whether the tracking system still identifies the markers as individual markers at a particular distance.

Any apparatus which comprises two markers and indicates the distance between the two markers can in principle be used as the calibration apparatus.

If the performance of the system which is to be expected is known, a user can simply set the marker distance on the apparatus 40 to the required minimum distance and—guided by a computer program which evaluates the tracking system output—can verify whether the system is capable of identifying two markers in a predetermined range within the calibrated volume. If this is not the case, the system has most probably been decalibrated. The user can also determine the extent of the calibration error by moving the markers further apart and then reading off the indicated measurement at which two markers are detected.

Figure 8:
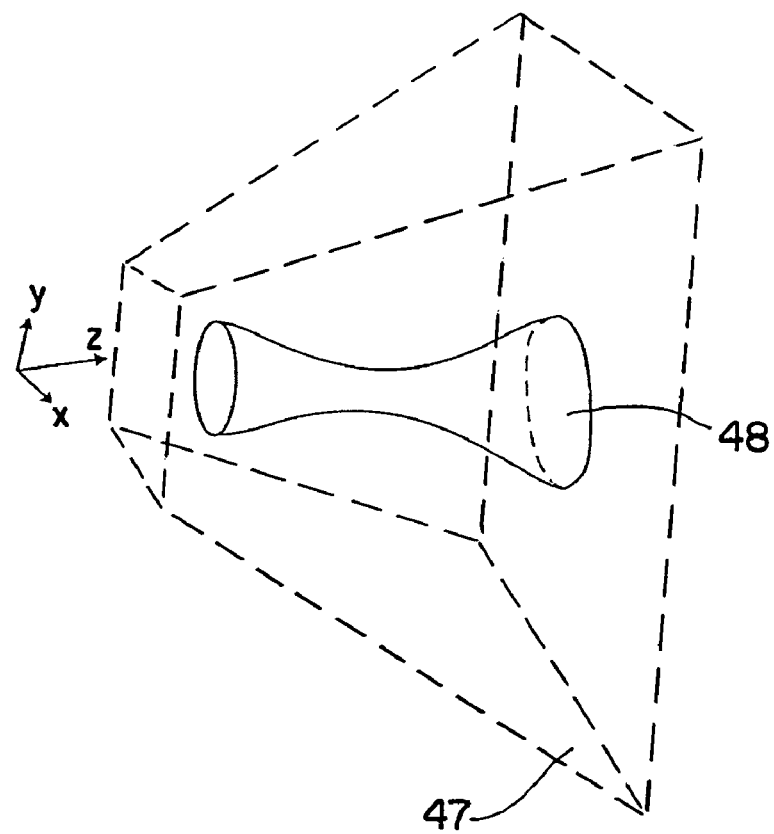
FIG. 8 a representation which shows a minimum distance volume in the detection range of the tracking system.

FIG. 8 shows the detection range 47 of a tracking system, together with the area co-ordinates X and Y and the depth co-ordinate Z. If it is assumed that tracking systems have similar or identical resolutions in the X direction and Y direction, the expectation would be that an elliptical or circular shape is created for the minimum distance mentioned, with a minimum diameter which typically lies approximately at the centre (Z axis) of the calibrated volume. Reference sign 48 in FIG. 8 shows a typical shape of a field for the minimum distance.

In order to obtain even more information about the calibration status of the tracking system, the position (specifically, the Z position) for the minimum diameter can be determined in the tracking volume. If the minimum position is known (by specifying the system or by previous determination), it is easy to assess whether changes have occurred which may affect the accuracy.

The invention claimed is:

1. A method for verifying a calibration status of an optical tracking system, comprising:
   moving a calibration apparatus, which comprises a plurality of tracking markers, within a detection range of the tracking system;

using the tracking system to detect the plurality of tracking markers;

changing an arrangement of the plurality of tracking markers relative to each other to a state that causes the tracking system to experience a detection problem;

determining the arrangement of the tracking markers that causes the detection problem; and concluding the tracking system has a calibration error when the arrangement that causes the detection problem does not correspond to a predetermined value or is not within a predetermined range of values.

2. The method according to claim 1, wherein determining the arrangement comprises using a measuring device assigned or attached to the calibration apparatus.

3. The method according to claim 2, wherein determining the arrangement comprises directly obtaining the arrangement from the measuring device or the calibration apparatus from scales or value indicators arranged on the calibration apparatus.

4. The method according to claim 1, wherein determining the arrangement comprises measuring at least one of distances or geometric relationships between the plurality of tracking markers.

5. The method according to claim 1, wherein determining the arrangement comprises determining an arrangement of the plurality of tracking markers relative to each other or a configuration of the plurality of tracking markers.

6. The method according to claim 1, wherein experiencing a detection problem comprises the occurrence of ambiguities in detecting markers, wherein a number of detected potential tracking markers is greater than an actual number of tracking markers present in the detection range.

7. The method according to claim 6, wherein changing the arrangement of the plurality of tracking markers relative to each other to the state that causes the tracking to system experience a detection problem comprises setting the arrangement such that the tracking markers are situated substantially in an epipolar plane of the tracking system.

8. The method according to claim 7, further comprising:
pivoting the plurality of tracking markers substantially perpendicular to the epipolar plane; and
using the measuring device to determine an angular range within which the ambiguities occur, wherein when the angular range is greater than a predetermined angular range, the tracking system is determined to have a calibration error.

9. The method according to claim 1, wherein experiencing a detection problem comprises insufficient resolution of individual markers during the determining step such that only a single marker is detected for two actual markers.

10. The method according to claim 9, wherein moving the calibration apparatus comprises moving the calibration apparatus to a predetermined point within the detection range of the tracking system.

11. The method according to claim 9, wherein changing the arrangement of the plurality of tracking markers comprises:
changing the arrangement such that a distance between the tracking markers is reduced; and
using the measuring device to determine the distance between the tracking markers at which the individual resolution is insufficient, wherein if the determined distance is greater than a predetermined maximum distance, the tracking system is determined to have a calibration error.

12. A device for verifying a calibration status of an optical tracking system, comprising:
a calibration apparatus including a plurality of tracking markers;
a tracking marker movement device operatively coupled to the plurality of tracking markers and configured to change a position of the plurality of tracking markers relative to each other;
a measuring device configured to detect the position of the plurality of tracking markers relative to each other; and
an evaluation unit configured to
compare the detected position of the plurality of tracking markers to a predetermined value or a predetermined range of values, and
ascertain the calibration status based on the comparison.

13. The device according to claim 12, wherein the measuring device is assigned or attached to the calibration apparatus.

14. The device according to claim 12, wherein the measuring device comprises a display on which the detected position of the plurality of tracking markers can be displayed, and wherein the calibration apparatus comprises scales or value indicators for obtaining the arrangement of the tracking markers.

15. The device according to claim 12, wherein the measuring device is configured to measure at least one of distances or angular positions of the plurality of tracking markers relative to each other.

16. The system according to claim 12, wherein the evaluation unit is configured to detect a detection problem defined as the occurrence of ambiguities in detecting markers, wherein the number of detected potential tracking markers is greater than the number of actual tracking markers present in a detection range of a tracking system.

17. The device according to claim 16, further comprising:
a mount, wherein the tracking markers are attached to the mount at a distance from each other, the mount pivotally arranged on the calibration apparatus; and
an angular scale arranged on the calibration apparatus and configured to indicate a pivoting angle of the mount.

18. The device according to claim 12, wherein the evaluation unit is configured to detect a detection problem defined as the occurrence of an insufficient resolution of individual markers when detecting markers, wherein for two tracking markers which are actually present in a detection range of a tracking system the tracking system only detects a single marker as being present.

19. The device according to claim 18, further comprising:
a mount, wherein the tracking markers are attached to the mount and spaced apart from each other; and
an adjusting device configured to change the spacing between the tracking markers.

20. The device according to claim 18, wherein the calibration apparatus comprises a rail, and at least one tracking marker of the plurality of tracking markers is configured to be movable on the rail, wherein a spacing between the plurality of tracking markers is measured on the basis of a displacement path of the at least one tracking marker on the rail.

* * * * *